United States Patent [19]

Patterson

[11] Patent Number: 4,662,361

[45] Date of Patent: May 5, 1987

[54] PHYSICAL THERAPY CHAIR

[76] Inventor: Merrill Patterson, 568 E. 4th St., Russellville, Ky. 42276

[21] Appl. No.: 776,446

[22] Filed: Sep. 16, 1985

[51] Int. Cl.[4] .............................................. A61F 13/00

[52] U.S. Cl. ................................ 128/25 R; 128/134; 128/70

[58] Field of Search ............... 297/195, 391, 172, 397, 297/411; 272/144, 93, 134; 128/25 R, 133, 134, 68-71; 269/322, 325, 328; D6/373

[56] References Cited

U.S. PATENT DOCUMENTS

| | | | |
|---|---|---|---|
| D. 265,610 | 8/1982 | Gusrud et al. | D6/373 |
| 1,111,685 | 9/1914 | Allison | 297/391 |
| 1,721,221 | 7/1929 | Jauregui | 297/411 |
| 2,944,592 | 7/1960 | Halter | 272/134 |
| 3,220,771 | 11/1965 | Doss, Sr. | 297/411 |
| 3,544,161 | 12/1970 | Bryden | 297/391 |
| 3,754,787 | 8/1973 | Garber | 297/195 |
| 3,949,983 | 4/1976 | Tommasino | 272/144 |
| 4,215,680 | 8/1980 | Okuda | 128/25 R |
| 4,313,639 | 2/1982 | Ware | 297/195 |

*Primary Examiner*—Richard J. Apley
*Assistant Examiner*—H. Macey
*Attorney, Agent, or Firm*—Harvey B. Jacobson

[57] ABSTRACT

An elongated base is provided including front and rear ends and the rear end includes an elevated seat portion. The forward end of the base includes upright standard projecting upwardly to a level above the seat and a rearwardly and upwardly inclined support arm is mounted from the upper end of the standard. The rear upper end of the support arm includes a rearwardly facing chest pad in general vertical registry with and spaced above the forward marginal edge of the seat. The support arm is mounted from the standard for forward and upward swinging of the rear end of the support arm from a lower limit position thereof and the support arm additionally supports a head (forehead) rest supported therefrom at an elevation above the chest pad and mounted from the support arm for front to rear adjustment relative to the chest pad.

11 Claims, 6 Drawing Figures

PHYSICAL THERAPY CHAIR

BACKGROUND OF THE INVENTION

1. Field of the Invention

This invention relates to a chair upon which a patient experiencing back pain may be seated with the patient's back in a forwardly and upwardly inclined position and the patient in as comfortable a position as is possible while the patient's spine and/or back is administered physical therapy.

2. Description of Related Art

Various different forms of patient chairs including some of the general structural and operational features of the instant invention heretofore have been designed. Examples of these previously known chairs are disclosed in U.S. Pat. Nos. 1,721,221, 3,220,771, 3,544,161, 3,754,787 and U.S. Pat. Des. No. 265,610. However, these previously known forms of chairs do not incorporate the overall combination of structural features of the instant invention which enables a patient maximum comfort as well as ease of assuming and rising from a seated position on the chair of the instant invention.

SUMMARY OF THE INVENTION

The therapy chair is constructed in a manner to enable a patient with back pain to assume as comfortable a position as possible to enable a therapist to perform back or spine therapy on the patient. The chair is further constructed in a manner whereby a patient in pain may assume and rise from a seated position on the chair with a minimum of pain to thereby eliminate the pain which many back patients must incur while trying to assume and arise from a prone position on a horizontal therapy table.

The main object of this invention is to provide a physical therapy chair upon which a patient to undergo back or spine therapy may be seated in a comfortable manner.

Another object of this invention is to provide a therapy chair constructed in a manner to enable a patient seated thereon to assume a position with his or her back in a forwardly and upwardly inclined position and with the muscles of the back relaxed.

Yet another important object of this invention is to provide a physical therapy chair in accordance with the preceding objects and to construct it in a manner enabling a patient to assume and rise from a seated position on the chair with a minimum amount of pain.

A further object of this invention is to provide a physical therapy chair including adjustment features thereof enabling the chair to be adjusted according to the stature of the patient to use the chair.

A final object of this invention to be specifically enumerated herein is to provide a physical therapy chair in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
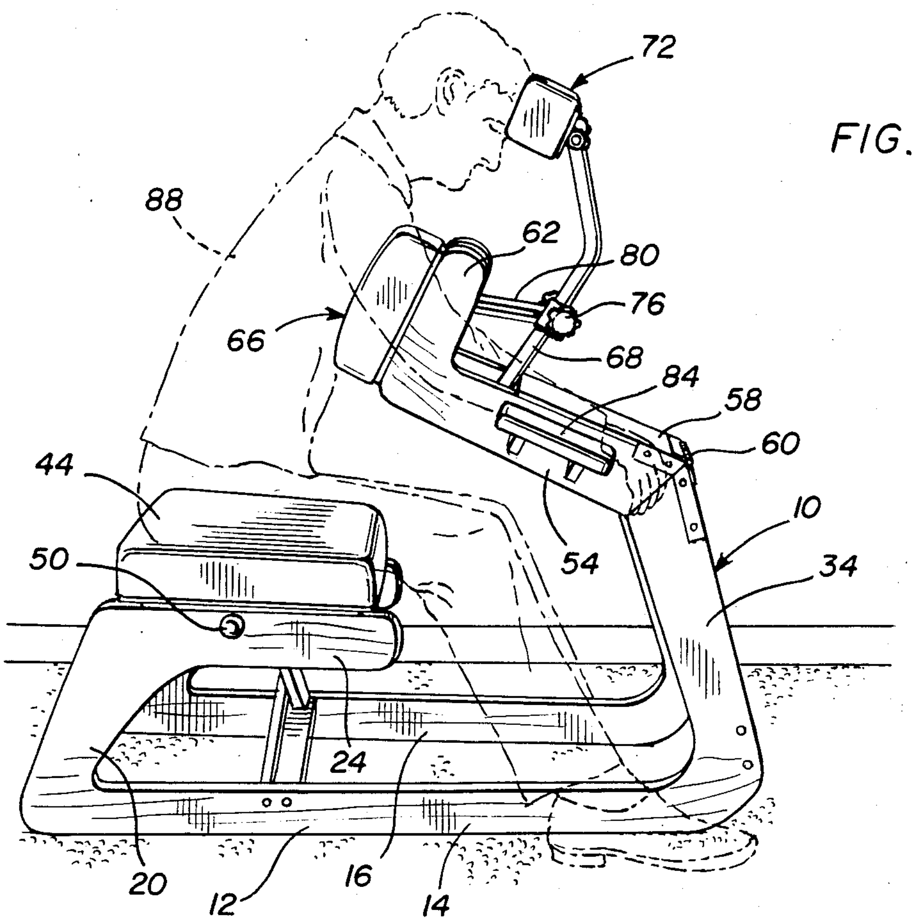
FIG. 1 is a right side perspective view of the physical therapy chair of the instant invention.
Figure 2:
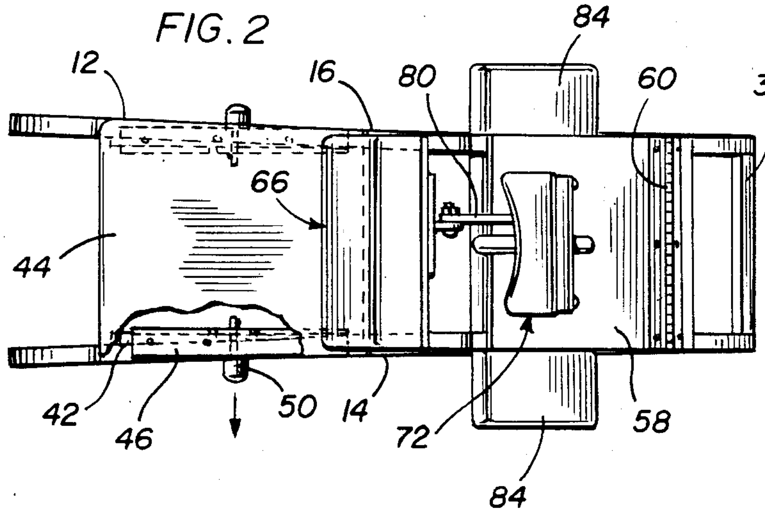
FIG. 2 is a top plan view of the physical therapy chair with a portion of the seat thereof broken away to illustrate the manner in which the seat may be adjustably shifted in fore and aft directions.
Figure 3:
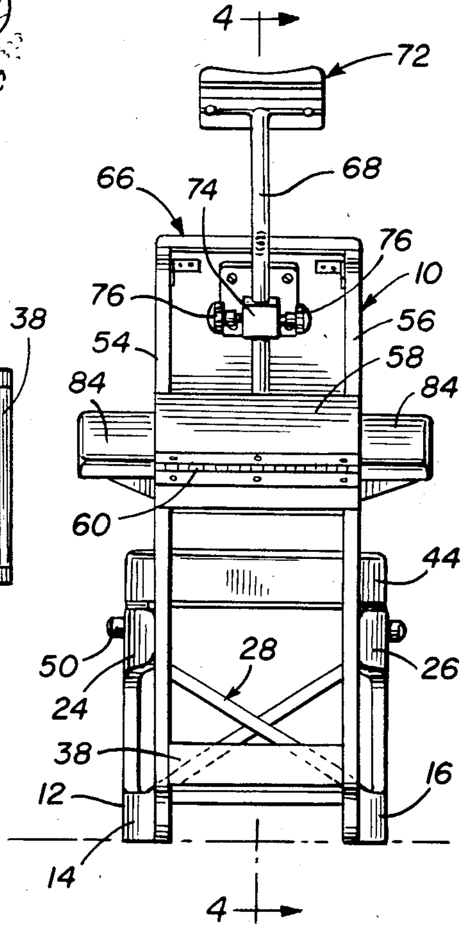
FIG. 3 is a front elevational view of the therapy chair.

Referring now more specifically to the drawings, the numeral 10 generally designates the therapy chair of the instant invention. The therapy chair 10 includes a horizontally elongated base 12 comprising a pair of low, step-over height and laterally spaced apart opposite side members 14 and 16 rigidly interconnected by a transverse brace 18 extending and secured between the members 14 and 16 at a point spaced approximately one-third the length of the members 14 and 16 forward of the rear ends thereof.

The rear ends of the members 14 and 16 include forwardly and upwardly inclined supports 20 and 22 formed integrally therewith and terminating at their upper ends in forwardly and horizontally directed support arms 24 and 26. A cross brace assembly referred to in general by the reference numeral 28 incorporating a pair of crossed bracing members 30 and 32 extends between the brace 18 and the support arms 24 and 26. Also, the forward ends of the members 14 and 16 include rearwardly and upwardly inclined supports 34 and 36 with a horizontal transverse brace 38 extending and secured between the lower ends of the supports 34 and 36 and a horizontal transverse brace 40 extending and secured between the upper ends of the supports 34 and 36.

Figure 4:
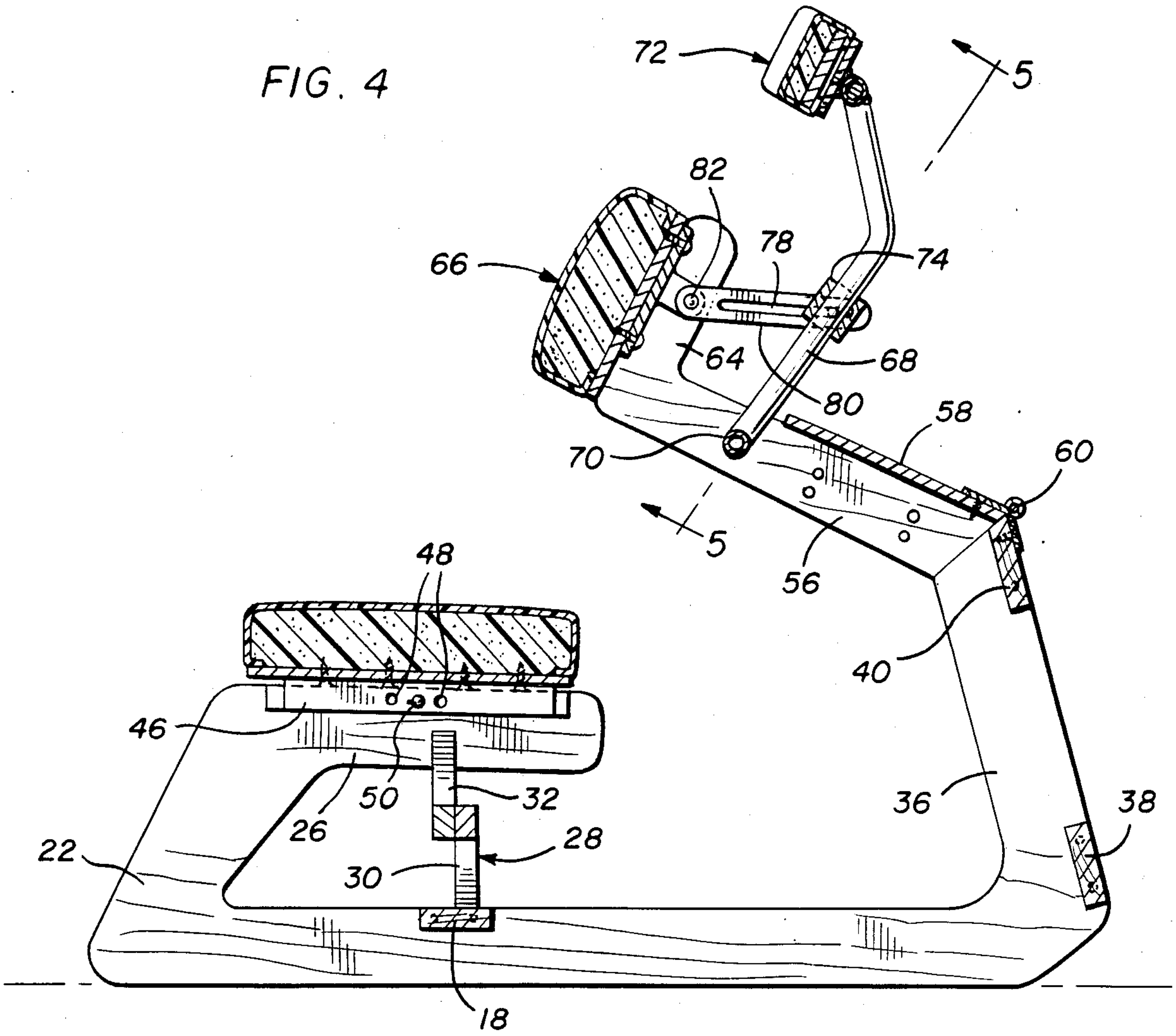
FIG. 4 is an enlarged vertical sectional view taken substantially upon the plane indicated by the section line 4—4 FIG. 3.
Figure 5:
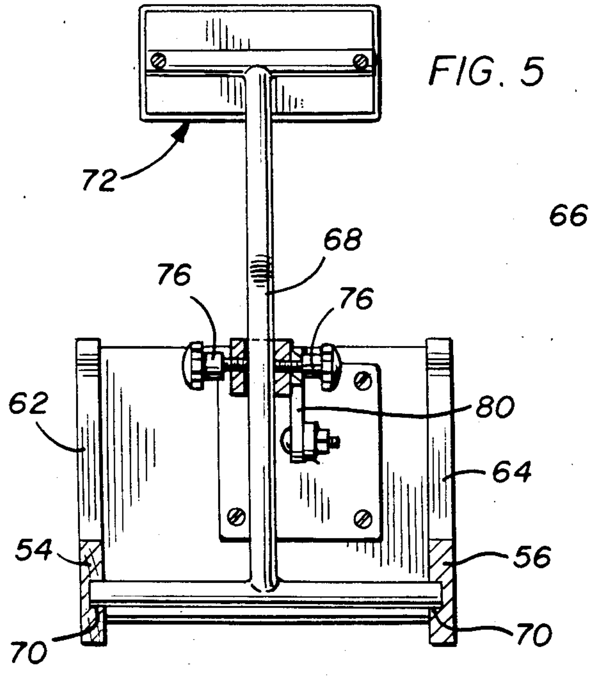
FIG. 5 is a sectional view taken substantially upon the plane indicated by the section line 5—5 of FIG. 4.

From FIGS. 1 and 4 of the drawings it may be seen that the member 14, the supports 20 and 34 and the support arm 24 comprise a right side frame of the chair 10 and that the member 16, supports 22 and 36 and support arm 26 comprise a right side frame of the chair 10, the side frames, as well as the bracing extending therebetween, being constructed of wood.

A pair of wedges 42 are secured to the inner sides of the support arms 24 and 26 and a seat construction 44 is provided and has opposite side angle members 46 secured to its undersurface and received between the wedges 42. The angle members 46 are provided with longitudinally spaced horizontal transverse apertures 48 and each of the support arms 24 and 26 is provided with a single transverse aperture with which the corresponding apertures 48 may be registered. A removable headed pin 50 is passed through each of the apertures in the support arms 24 and 26 and through a selected aperture 48 in the corresponding angle member 46 in order to retain the seat construction 44 in adjusted fore and aft shifted position relative to the support arms 24 and 26.

The upper ends of the supports 34 and 36 have the lower ends of a pair of rearwardly and upwardly-inclined support arms 54 and 56 pivotally secured thereto. The lower ends of the support arms 54 and 56 are rigidly interconnected by a transverse inclined bracing panel 58 extending and secured between the lower portions of the upper marginal edges of the support arms and a piano hinge 60 has its leaves anchored to the brace 40 and the panel 58.

The rear upper ends of the support arms 54 and 56 terminate rearwardly in upwardly directed right-angled mounting arms 62 and 64 from whose rear upstanding edges a chest pad assembly referred to in general by the reference numeral 66 is secured. An upstanding arm 68 has its lower end pivotally secured between the upper end portions of the support arms 54 and 56 as at 70 and the upper end of the arm 68 supports a forehead pad assembly referred to in general by the reference numeral 72. A sleeve 74 is slidable on the lower end of the arm 68 and includes a pair of opposite side setscrews 76 threadingly supported therefrom and including inner ends engageable with the arm 68. In addition, one of the setscrews 76 is slightly longer than the other setscrew 76 and passes through the center longitudinal slot 78 formed in an elongated brace arm 80 having one end thereof pivotally mounted from the chest pad assembly 66 as at 82. By loosening the setscrews 76 the sleeve 74 may be shifted longitudinally of the lower end of the arm 68 and the brace arm 80 may be shifted longitudinally relative to the sleeve 74. In this manner, the arm 68 may be angularly adjusted as desired and retained in adjusted positioning by tightening the setscrew 76.

The entire pivoted assembly comprising the support arms 54 and 56 may be swung about a horizontal transverse axis defined by the piano hinge 60. The lower limit position of the assembly is illustrated in FIG. 4 and the upper portion thereof may be swung forwardly and upwardly in the manner illustated in FIG. 6 of the drawings. Furthermore, each of the support arms 54 and 56 includes an outer side armrest 84 supported therefrom.

Figure 6:
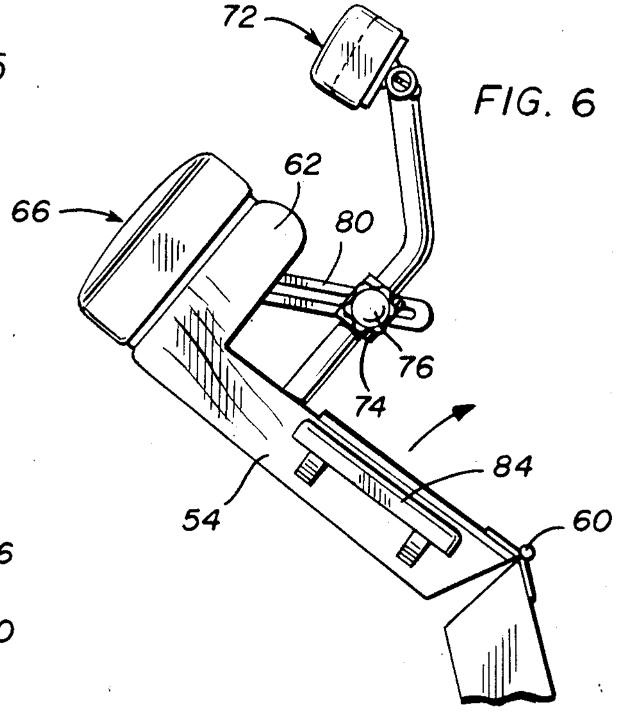
FIG. 6 is a fragmentary side elevational view of the upper forward portion of the chair illustrating the manner in which the chest pad and the head pad supporting portion of the chair may be swung forwardly and upwardly to an out-of-the-way position in order to enable a patient to more readily be seated upon and rise from the chair.

With attention now invited more specifically to FIGS. 1 and 6 of the drawings, the assembly comprising the interconnected support arms 54 and 56 may be swung upwardly from the position thereof illustrated in FIG. 4 to the position illustrated in FIG. 6 (and beyond) and thus render it quite easy for a patient 88 experiencing back or spinal pain to assume a seated position upon the seat construction 44 after the latter has been adjusted in a fore and aft direction as desired. Thereafter, the assembly comprising the interconnected support arms 54 and 56 may be swung back to the limit position thereof illustrated in FIG. 4 and the forehead pad assembly 72 may be adjusted so that the patient 88 may assume the most comfortable position while having therapy applied to his or her back or spine.

The seat construction 44 is adjustable in a fore and aft direction in order that the position of the seat construction 44 may be adjusted relative to the chest pad assembly 66 and the forehead pad assembly 72 may be adjusted in a fore and aft direction relative to the chest pad assembly 66.

The chair 10 enables the patient 88, when experiencing pain, to assume and rise from a position on the seat constructin with minimal pain. Further, therapy may be applied to the back and spine of the patient 88 while the patient is seated on the chair 10 in as comfortable a position as possible. Use of the chair 10 has been found to be considerably more comfortable and less painful to a patient than having that patient assume a prone position on the usual horizontal therapy table and to thereafter attempt to rise from a prone position on the therapy table.

The chair 10, except for various hardware features thereof, is constructed of wood or fiber glass to thereby enable electrical therapy treatments to be carried out with maximum safety.

The foregoing is considered as ilustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A physical therapy chair including a horizontally elongated base defining front and rear ends, a horizontal seat, mounting means mounting said seat from said rear end in elevated position relative thereto, said front end including upstanding standard means, a rearwardly and upwardly inclined support arm including upper and lower ends, pivot means pivotally mounting the lower end of said support arm from the upper portion of said standard for angular displacement relative thereto about a horizontal axis extending transversely of said support arm and standard between a lowered limit position with said arm rearwardly and upwardly inclined and a raised position with said upper end of said support arm swung upwardly and forwardly from said lower limit position thereof, said upper end of said support arm supporting a rearwardly facing chest pad therefrom disposed at a predetermined chest height elevation spaced generally vertically above the forward marginal portion of said seat when said support arm is in said lowered limit position, said base including generally horizontal low, step-over height and laterally spaced opposite side longitudinal members adapted to rest upon a floor surface, said standard means comprising a pair of opposite side upstanding supports supporting and projecting upwardly from the front end portions of said longitudinal members, said support arm comprising a pair of opposite side inclined support arms having their lower ends pivotally supported from the upper ends of said upstanding supports by said pivot means, said chest pad being supported from connecting means extending between and connecting the upper ends of said support arms, said seat being spaced sufficiently rearward of said upstanding supports to define a lower leg receiving area above said opposite side members between said seat and upstanding supports for passage of a user's leg laterally of said base from one side thereof into said area when a user is assuming or arising from a seated position on said seat, said support arms being elevated above said seat and extending rearwardly from said upstanding supports to a position spaced generally vertically above at least the forward portion of said seat in order to provide knee clearance in said area for a user seated on said seat.

2. The physical therapy chair of claim 1 including a rearwardly facing headrest mounted from said support arm in elevated position relative to said chest pad and adjustable in a fore and aft direction relative to said chest pad.

3. The physical therapy chair of claim 1 wherein said arm includes a pair of horizontally registered and laterally spaced apart arm members, the remote sides of said arm members including laterally outwardly projecting forearm rests extending longitudinally therealong.

4. The physical therapy chair of claim 1 wherein said said mounting means includes means mounting said seat from said rear end for adjustable fore and aft positioning along said base, said elongated base including a pair of laterally spaced longitudinally extending opposite side base members, said standard means including upwardly projecting opposite side standard members mounted from the forward end portions of said base members, said mounting means including a second pair of opposite side standard members supported and projecting upwardly from the rear ends of said base members.

5. The physical therapy chair of claim 4 wherein the upper ends of said second pair of standard members include forwardly projecting support arms from which said seat is supported.

6. The physical therapy chair of claim 5 including a rearwardly facing headrest mounted from said support arm in elevated position relative to said chest pad and adjustable in a fore and aft direction relative to said chest pad.

7. A physical therapy chair including a horizontally elongated base defining front and rear ends, a horizontal seat, mounting means mounting said seat from said from said rear end in elevated position relative thereto, said front end including upstanding standard means, a rearwardly and upwardly inclined support arm including upper and lower ends, pivot means pivotally mounting the lower end of said support arm from the upper portion of said standard for angular displacement relative thereto about a horizontal axis extending transversely of said support arm and standard between a lowered limit position with said arm rearwardly and upwardly inclined and a raised position with said upper end of said support arm swung upwardly and forwardly from said lower limit position thereof, said upper end of said support arm supporting a rearwardly facing chest pad therefrom disposed at a predetermined chest height elevation spaced generally vertically above the forward marginal portion of said seat when said support arm is in said lowered limit position, said mounting means including means mounting said seat from said rear end for adjustable fore and aft positioning along said base.

8. The physical therapy chair of claim 7 including a rearwardly facing headrest mounted from said support arm in elevated position relative to said chest pad and adjustable in a fore and aft direction relative to said chest pad.

9. A physical therapy chair including a horizontally elongated base defining front and rear ends, a horizontal seat, mounting means mounting said seat from said rear end in elevated position relative thereto, said front end including upstanding standard means, a rearwardly and upwardly inclined support arm including upper and lower ends, pivot means pivotally mounting the lower end of said support arm from the upper portion of said standard for angular displacement relative thereto about a horizontal axis extending transversely of said support arm and standard between a lowered limit position with said arm rearwardly and upwardly inclined and a raised position with said upper end of said support arm swung upwardly and forwardly from said lower limit position thereof, said upper end of said support arm supporting a rearwardly facing chest pad therefrom disposed at a predetermined chest height elevation spaced generally vertically above the forward marginal portion of said seat when said support arm is in said lowered limit position, said elongated base including a pair of laterally spaced longitudinally extending opposite side base members, said standard means including upwardly projecting opposite side standard members mounted from the forward end portions of said base members, said mounting means including a second pair of opposite side standard members supported and projecting upwardly from the rear ends of said base members, the upper ends of said second pair of standard members including forwardly projecting support arms from which said seat is supported.

10. The physical therapy chair of claim 9 wherein said mounting means includes means mounting said seat from said rear end for adjustable fore and aft positioning along said base.

11. The physical therapy chair of claim 10 wherein said arm includes a pair of horizontally registered and laterally spaced arm members, the remote sides of said arm members including laterally outwardly projecting forearm rests extending longitudinally therealong.

* * * * *